(12) United States Patent
Leiba et al.

(10) Patent No.: US 9,782,387 B2
(45) Date of Patent: Oct. 10, 2017

(54) COMPOSITIONS AND METHODS FOR TREATING HEMATOLOGICAL MALIGNANCIES

(71) Applicant: Tel HaShomer Medical Research Infrastructure and Services Ltd., Ramat-Gan (IL)

(72) Inventors: Merav Leiba, Ramat-Gan (IL); Gabriela Rozic, Hod-HaSharon (IL)

(73) Assignee: Tel HaShomer Medical Research Infrastructure and Services Ltd., Ramat-Gan (IL)

( * ) Notice: Subject to any disclaimer, the term of this patent is extended or adjusted under 35 U.S.C. 154(b) by 0 days.

(21) Appl. No.: 15/101,079

(22) PCT Filed: Oct. 29, 2014

(86) PCT No.: PCT/IL2014/050936
§ 371 (c)(1),
(2) Date: Jun. 2, 2016

(87) PCT Pub. No.: WO2015/097691
PCT Pub. Date: Jul. 2, 2015

(65) Prior Publication Data
US 2016/0303080 A1    Oct. 20, 2016

Related U.S. Application Data

(60) Provisional application No. 61/964,168, filed on Dec. 26, 2013.

(51) Int. Cl.
*A61K 31/404* (2006.01)
*A61K 45/06* (2006.01)
*C07D 405/04* (2006.01)

(52) U.S. Cl.
CPC ............ *A61K 31/404* (2013.01); *A61K 45/06* (2013.01); *C07D 405/04* (2013.01)

(58) Field of Classification Search
CPC .. A61K 31/404; A61K 2300/00; A61K 45/06; C07D 405/04
See application file for complete search history.

(56) References Cited

U.S. PATENT DOCUMENTS

| 2003/0105038 A1 | 6/2003 | Monia et al. |
| 2007/0078085 A1 | 4/2007 | Chung et al. |
| 2008/0076737 A1* | 3/2008 | Ossovskaya ............ A61K 31/12 514/75 |

(Continued)

FOREIGN PATENT DOCUMENTS

| WO | WO2011073929 | * | 6/2011 | ............ A61K 31/404 |
| WO | WO 2015/097691 | | 7/2015 | |

OTHER PUBLICATIONS

International Preliminary Report on Patentability dated Jul. 7, 2016 From the International Bureau of WIPO Re. Application No. PCT/IL2014/050936.

(Continued)

*Primary Examiner* — Savitha Rao

(57) ABSTRACT

A compound represented by Formula I is provided for use in the treatment of a hematological malignancy in a subject in need thereof. Also provided are compositions and kits which comprise the compound.

8 Claims, 6 Drawing Sheets
(4 of 6 Drawing Sheet(s) Filed in Color)

6-(furan-2-yl)-3-methyl-4-oxo-1,5,6,7-tetrahydroindole-2-carboxylate

(56) References Cited

U.S. PATENT DOCUMENTS

2014/0255341 A1  9/2014  Kalinski et al.
2014/0256776 A1  9/2014  Chen et al.

OTHER PUBLICATIONS

International Search Report and the Written Opinion dated Jan. 20, 2015 From the International Searching Authority Re. Application No. PCT/IL2014/050936.
Nguyen et al. "Evading Pgp Activity in Drug-Rsistant Cancer Cells: A Structural and Functional Study of Antitubulin Furan Metotica Compounds", Molecular Cancer Therapeutics, 11(5): 1103-1111, Published Online Mar. 21, 2012.
PubChem "ST50642100", PubChem Compound, 3 P., Nov. 9, 2014.
Supplementary European Search Report and the European Search Opinion dated Jun. 19, 2017 From the European Patent Office Re. Application No. 14875724.8. (9 Pages).
Rozic et al. "The Novel Compound STK405759 Is a Microtubule-Targeting Agent With Potent and Selective Cytotoxicity Against Multiple Myeloma in Vitro and in Vivo", Oncotarget, XP055379004, 7(38): 62572-62584, Aug. 23, 2016.

* cited by examiner

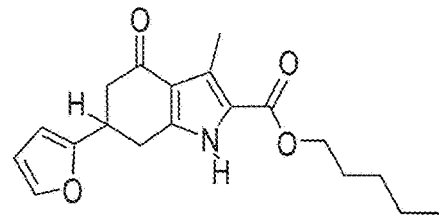
FIG. 1A
6-(furan-2-yl)-3-methyl-4-oxo-1,5,6,7-tetrahydroindole-2-carboxylate
FIG. 1B
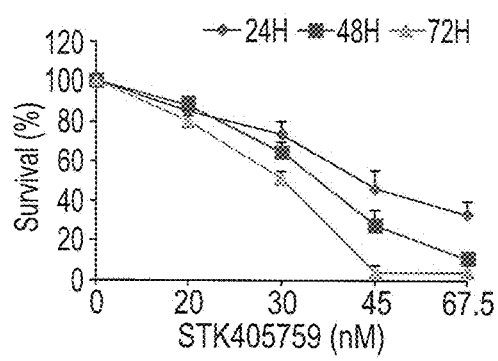
FIG. 1C
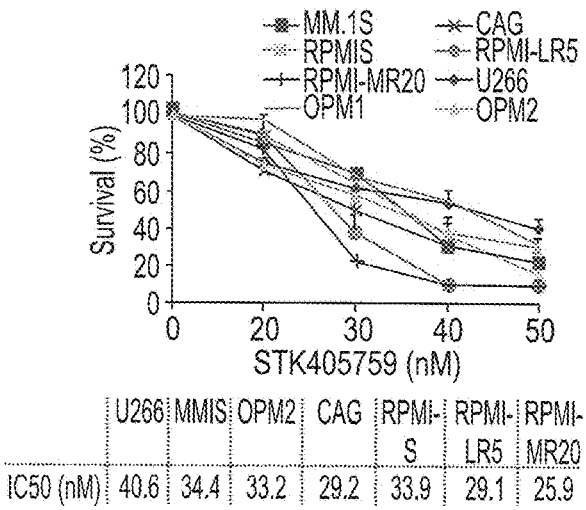
FIG. 1D
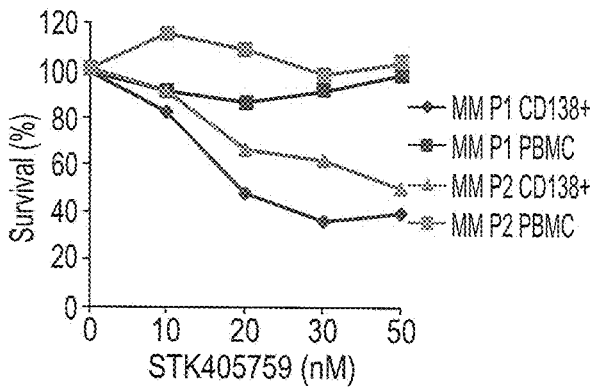
FIG. 1E
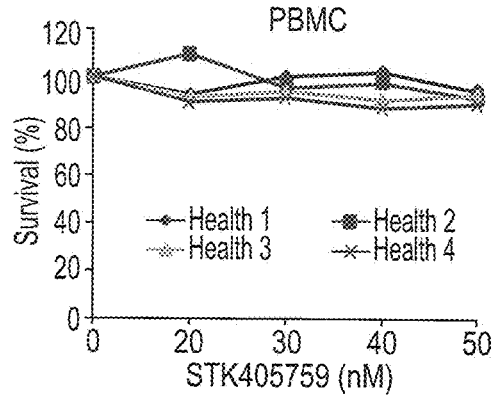

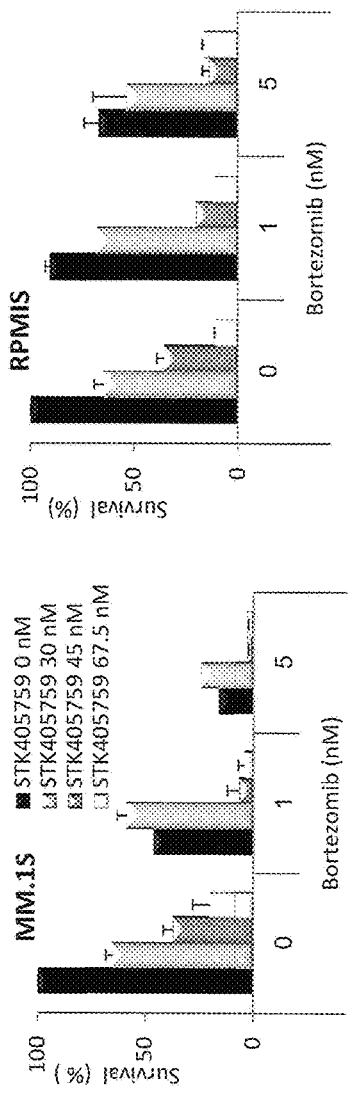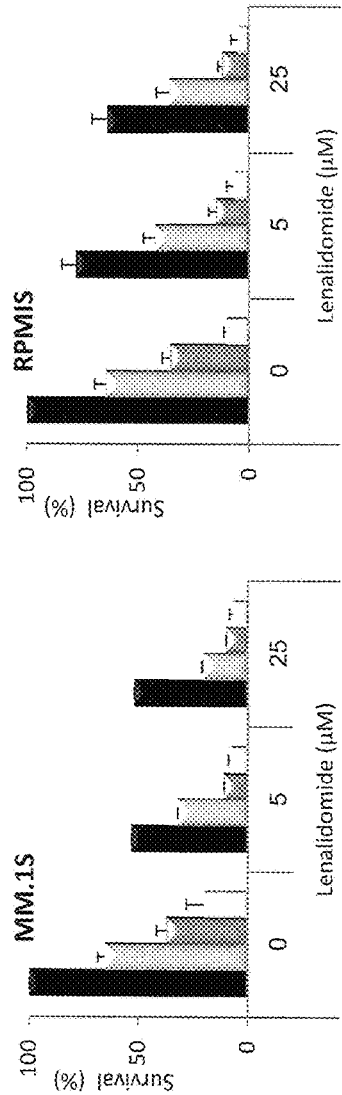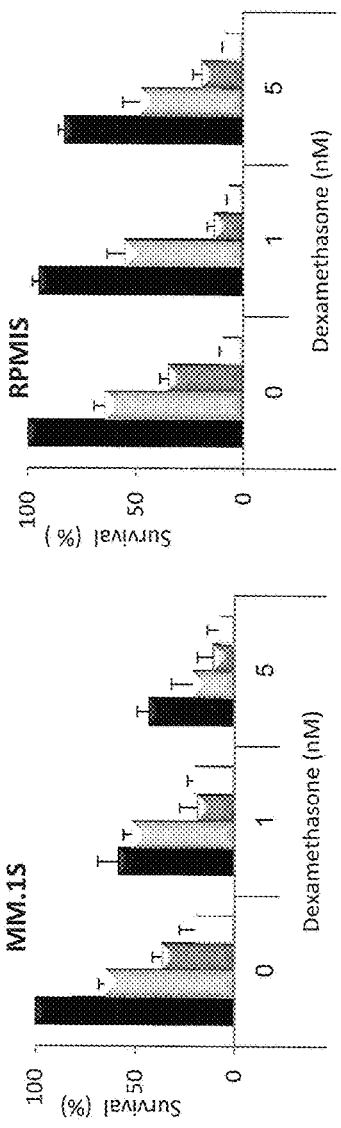
FIG. 5A
FIG. 5B
FIG. 5C

COMPOSITIONS AND METHODS FOR TREATING HEMATOLOGICAL MALIGNANCIES

RELATED APPLICATIONS

This application is a National Phase of PCT Patent Application No. PCT/IL2014/050936 having International filing date of Oct. 29, 2014, which claims the benefit of priority under 35 USC §119(e) of U.S. Provisional Patent Application No. 61/964,168 filed on Dec. 26, 2013. The contents of the above applications are all incorporated by reference as if fully set forth herein in their entirety.

FIELD AND BACKGROUND OF THE INVENTION

The present invention, in some embodiments thereof, relates to compositions and methods for treating hematological malignancies.

Hematological malignancies affect blood, bone marrow, and lymph nodes. These malignancies typically derive from either of the two major blood cell lineages: myeloid and lymphoid cell lines. The myeloid cell line normally produces granulocytes, erythrocytes, thrombocytes, macrophages and mast cells; the lymphoid cell line produces B. T. NK and plasma cells. Lymphomas, lymphocytic leukemias, and myeloma are from the lymphoid line, while acute and chronic myelogenous leukemia, myelodysplastic syndromes and myeloproliferative diseases are myeloid in origin. Taken together, haematological malignancies account for 9.5% of new cancer diagnoses in the United States and 30,000 patients in the UK are diagnosed each year. Within this category, lymphomas are more common than leukemias.

Multiple myeloma (MM) is a B-cell malignancy characterized by accumulation of plasma cells in the bone marrow, associated with end-organ damage that can include lytic bone lesions, anemia, immunodeficiency, and decreased renal function. MM accounts for 10% of all hematologic malignancies. It represents 1% of all cancer diagnoses, the most common malignant bone tumor and 2% of all cancer deaths [1-4].

Treatments utilizing cytotoxic chemotherapy, including alkylating agents, corticosteroids or high-dose chemotherapy followed by autologous stem cell transplantation, proteasome inhibitors and thalidomide analogues, have resulted in significant survival benefits, however, despite these advances, current therapies cannot eradicate the disease and relapses are frequently seen [5.6]. Although changes in the therapeutic landscape during the last 10-15 years have prolonged the median survival from 3 years to 6 years, the disease remains largely incurable [5,6].

For example, dexamethasone is a commonly used regimen for first-line treatment of MM. More recently, combinations of vincristine, doxorubicin, and dexamethasone (VAD) have been used to treat multiple myeloma. However, these are not effective long-term treatments. Dexamethasone treatment has a response rate of approximately 25-35%. In many patients, high-dose chemotherapy supported by autologous stem cell transplantation (ASCT) may prolong event-free survival if the procedure is performed within 12 months of initial diagnosis. However almost all patients receiving high-dose chemotherapy and an autologous peripheral stem cell transplant will ultimately relapse.

Hence, the pursuit for novel therapeutics against hematological malignancies in general and MM in particular is critically important.

RELATED ART

US 20140256776, US 20140255341, US 20070078085 and US 20030105038;

Xiao et al. Curr Cancer Drug Targets. Author manuscript; available in PMC Oct. 22, 2014; www(dot)pubchem(dot)ncbi(dot)nlm(dot)nih(dot)gov/summary/summary(dot)cgi?sid=58042434#ec.

SUMMARY OF THE INVENTION

According to an aspect of some embodiments of the present invention there is provided a compound represented by Formula I:

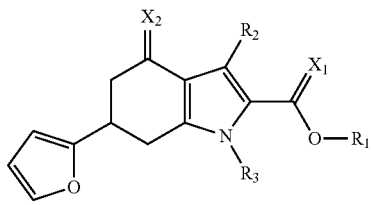

Formula I wherein:

$X_1$ and $X_2$ are each independently oxygen or sulfur;

$R_2$ and $R_3$ are each independently hydrogen or alkyl; and $R_1$ is alkyl, for use in the treatment of a hematological malignancy in a subject in need thereof.

According to an aspect of some embodiments of the present invention there is

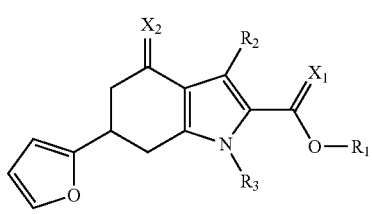

Formula I wherein:

$X_1$ and $X_2$ are each independently oxygen or sulfur;

$R_2$ and $R_3$ are each independently hydrogen or alkyl; and $R_1$ is alkyl, in the manufacture of a medicament identified for the treatment of a hematological malignancy.

According to an aspect of some embodiments of the present invention there is provided a method of treating a hematological malignancy in a subject in need thereof, the method comprising administering to the subject a therapeutically effective amount of a compound represented by Formula I:

Formula I wherein:
X₁ and X₂ are each independently oxygen or sulfur;
R₂ and R₃ are each independently hydrogen or alkyl; and
R₁ is alkyl,
thereby treating the hematological malignancy.

According to an aspect of some embodiments of the present invention there is provided an article of manufacture identified for the treatment of a hematological malignancy, comprising as active ingredients a compound represented by Formula I:

Formula I wherein:
X₁ and X₂ are each independently oxygen or sulfur;
R₂ and R₃ are each independently hydrogen or alkyl; and
R₁ is alkyl,
and a chemotherapy.

According to an aspect of some embodiments of the present invention there is provided a pharmaceutical composition comprising as an active ingredient a compound represented by Formula I:

Formula I wherein:
X₁ and X₂ are each independently oxygen or sulfur;
R₂ and R₃ are each independently hydrogen or alkyl; and
R₁ is alkyl,
and a pharmaceutically acceptable carrier or diluents.

According to some embodiments of the invention, the hematological malignancy is selected from the group consisting of myeloma, lymphoma, lymphocytic leukemia, acute and chronic myelogenous leukemia, myelodysplastic syndrome and myeloproliferative disease.

According to some embodiments of the invention, the hematological malignancy is characterized by overexpression and/or over-activation of cyclic-AMP response element-binding protein (CREB).

According to some embodiments of the invention, the hematological malignancy is characterized by chemoresistance.

According to some embodiments of the invention, the hematological malignancy is multiple myeloma.

According to some embodiments of the invention, the chemoresistance is for a chemotherapy selected from the group consisting of bortezomib (BTZ), lenalidomide (LEN) and dexamethasone (DEX).

According to some embodiments of the invention, the compound and the chemotherapy are in a co-formulation.

According to some embodiments of the invention, the compound and the chemotherapy are in separate containers.

According to some embodiments of the invention, the compound induces apoptosis of multiple myeloma cells optionally associated with the induction of caspase-8 and poly (ADP-ribose) polymerase cleavage.

According to some embodiments of the invention, the compound does not affect peripheral blood mononuclear cells.

According to some embodiments of the invention, the compound elicits G2 cell cycle arrest.

According to some embodiments of the invention, the composition down-regulates AKT and/or CREB protein expression.

According to some embodiments of the invention, the compound is provided as a pharmaceutical composition which further comprises a carrier.

According to some embodiments of the invention, the compound is 6-(furan-2-yl)-3-methyl-4-oxo-1, 5, 6, 7-tetrahydroindole-2-carboxylate:

According to some embodiments of the invention, each of X₁ and X₂ is oxygen.

According to some embodiments of the invention, R₂ is alkyl.

According to some embodiments of the invention, R₂ is methyl.

According to some embodiments of the invention, R₃ is hydrogen.

According to some embodiments of the invention, R₁ is an alkyl having 2-10 carbon atoms.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-E STK405759 induces cytotoxicity in MM cells. FIG. 1A shows the chemical structure of STK405759 FIGS. 1B-E—Viability of STK405759 treated cells was assessed by XTT assay in: FIG. 1B—RPMIS MM cells treated for 24, 48 and 72 hours, FIG. 1C a panel of MM cell lines treated for a period of 48 hours, FIG. 1D—freshly isolated MM cells from bone marrow aspirated of MM patients (MM P1 and P2), processed using Miltenyianti-CD138 microbeads and PBMCs from the same patients treated for a period of 48 hours, FIG. 1E—PBMCs from healthy donors treated for a period of 48 hours. Each treatment was performed in triplicates in three independent experiments (cell lines) and presented as means±SE. Values were normalized to the drug-free control.

Figure 2A:
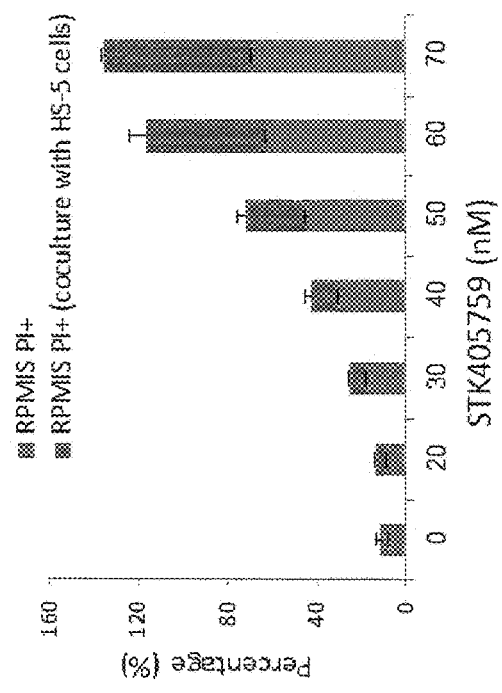
Figure 2B:
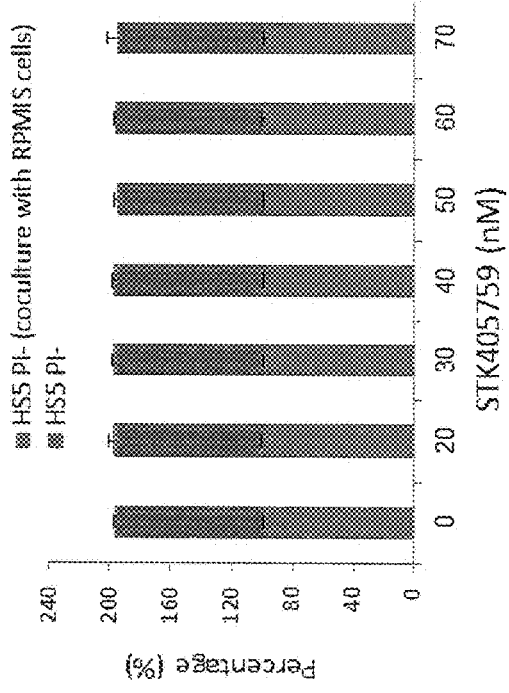
Figure 2C:
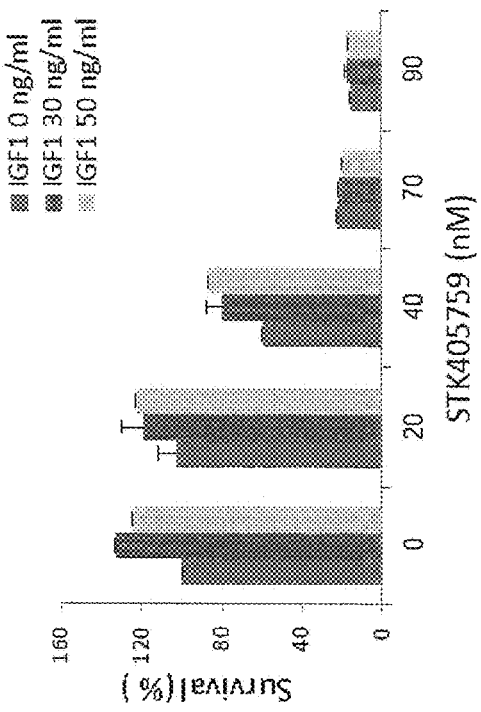
Figure 2D:
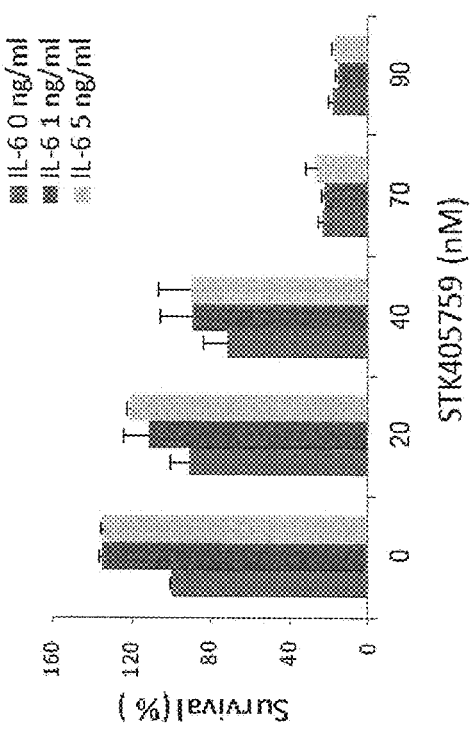

FIGS. 2A-D are graphs showing that STK405759 overcomes the growth stimulatory effect of BMSCs. IL-6 or IGF-1 on MM cell growth. FIG. 2A-B—RPMIS cells were stained with CFSE, co-cultured with HS-5 and exposed to STK405759 (70 nM) for 48 h. The cells were contrastained with PI to distinguish live from nonviable cells using FACS analysis. The values of the fraction of nonviable (CFSE$^-$PI$^+$) HS-5 cells within the entire population of HS-5 cells (CFSE$^-$) cultured alone or with RPMIS cells, and the fraction of (CFSE$^+$PI$^+$) RPMIS cells within the entire population of RPMIS cells (CFSE) cultured alone or with HS-5 cells are presented as a function of the STK405759 concentrations. FIGS. 2C-D—RPMIS cells were cultured for 48 hours at the indicated concentrations of STK405759 in the presence or absence of IL-6 (5 or 10 ng/ml) or IGF-1 (10 or 30 ng/ml). Data presented are from three independent experiments and presented as means±SE.

Figure 3B:
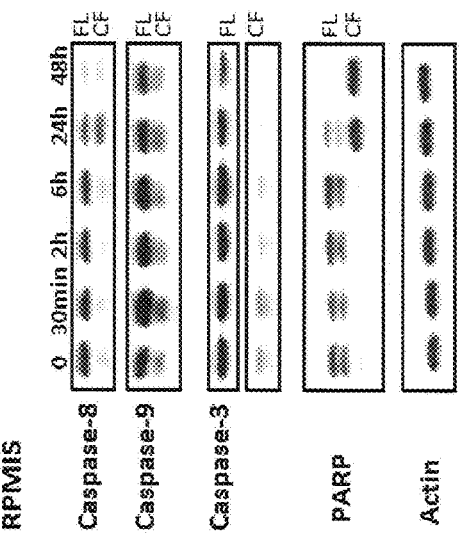
Figure 3D:
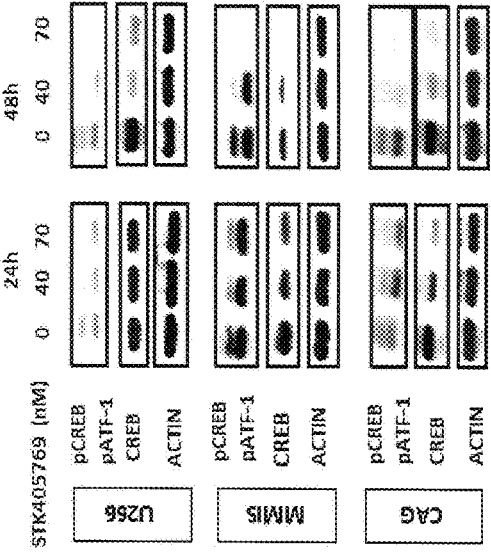
Figure 3A:
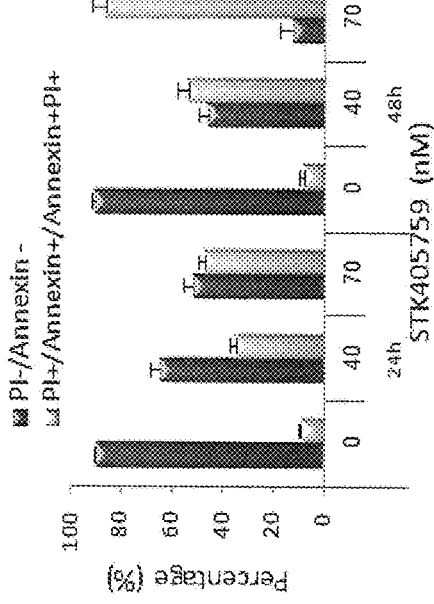

FIGS. 3A-D shows that STK405759 induces apoptosis and decreased AKT and CREB expression. FIG. 3A—RPMIS cells treated with STK405759 were analyzed for induction of apoptosis by APC Annexin V/PI assay. APC Annexin V+/PI− represent the percentage of cells in early apoptosis, APC Annexin V+/PI+ represents the percentage of cells in late apoptosis or necrosis. Lysates from RPMIS cells treated with STK405759 70 nM were immunoblotted using: anti caspase-3, -8, -9, PARP, and GAPDH antibodies (FIG. 3B). FL, CF indicates the full length and cleaved form, respectively and (FIG. 3C) anti-pAKT, AKT, p-CREB, CREB, Mcl-1, p42/44MEK, MEK and actin antibodies. FIG. 3D—the expression level of p-CREB and CREB was evaluated in U266, MM.1S and CAG MM STK405759 treated cells (n=2 independent experiments).

Figure 4A:
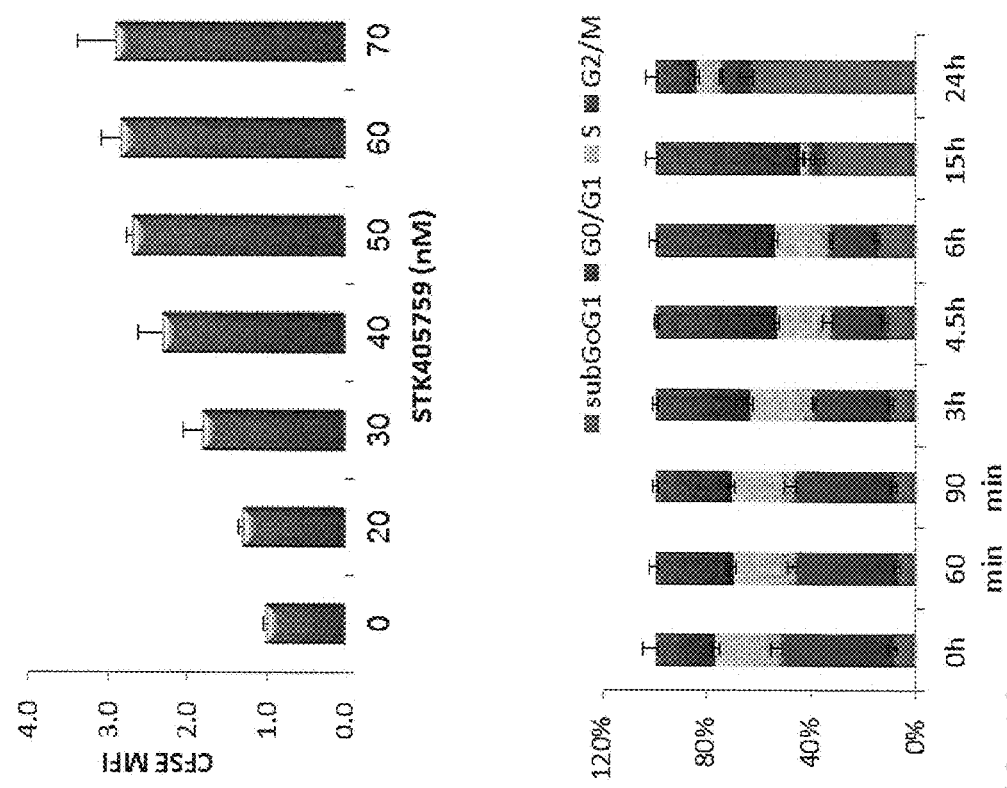
Figure 4B:
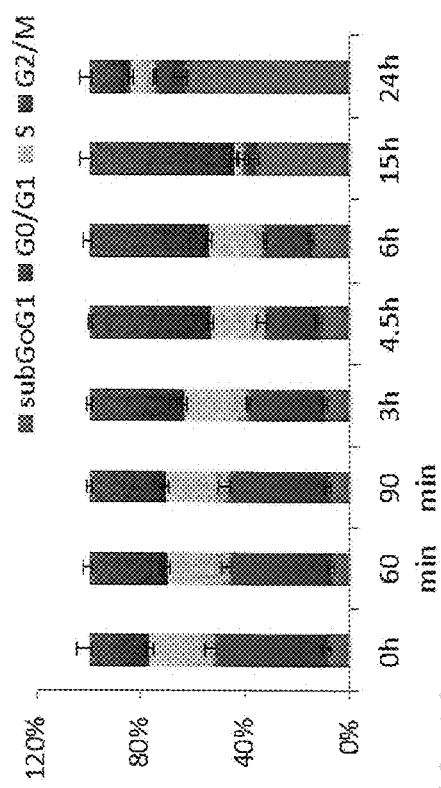
Figure 4C:
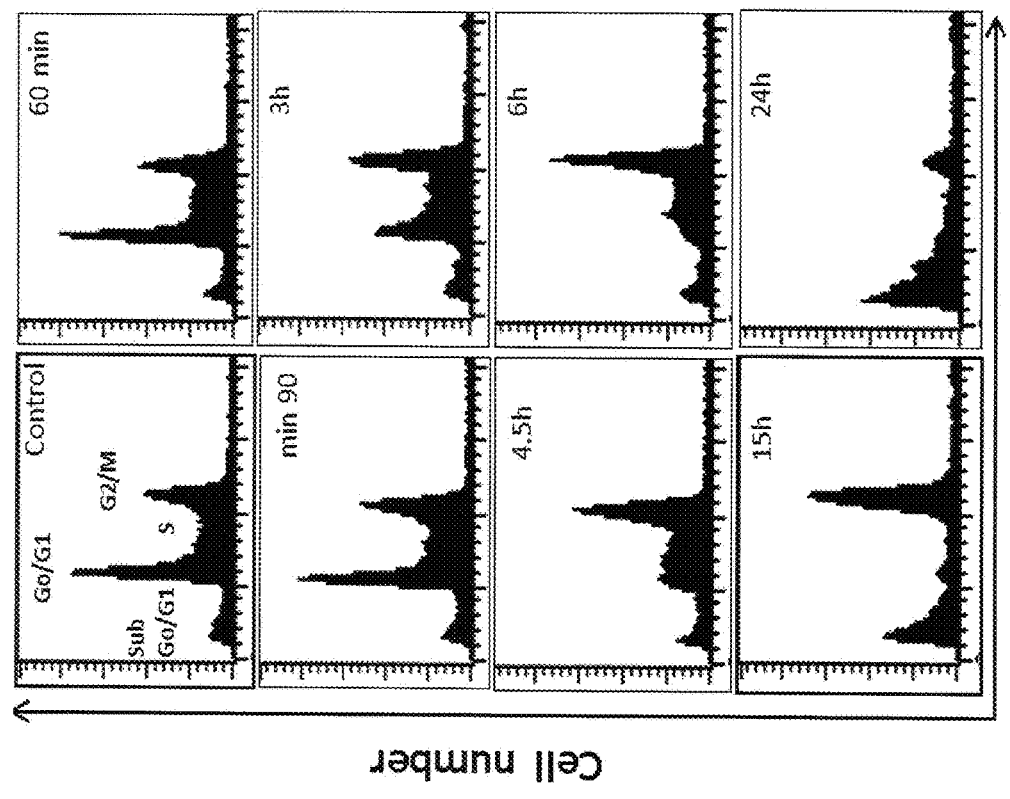

FIGS. 4A-C are graphs showing that STK405759 inhibits proliferation of MM cells. FIGS. 4A, C—RPMIS cells were treated with STK405759 (70 nM) for time points. Cell-cycle analysis showed initially an increase of cells in G2/M and then an increase in apoptosis (subG0/G1). FIG. 4B—Fluorescence intensity of CFSE$^+$ labelled RPMIS is shown as a function of STK405759 concentration (0-70 nM) relative to untreated control cells. Each treatment was performed in duplicate in three independent experiments and presented as means±SE. MFI: Mean fluorescent intensity.

FIGS. 5A-C are graphs showing the cytotoxic effect of STK405759 in combination with currently in use anti-MM drugs. MM.1S and RPMIS MM cells were treated with STK405759 (0, 30, 45 and 67.5 nM) in combination with (FIG. 5A) bortezomib (1 and 5 nM); (FIG. 5B) lenalidomide (5 and 25 µM) and (FIG. 5C) dexamethasone (1 and 5 nM) for 48 hours and their viability assessed by XTT assay. Each treatment was performed in triplicates in three independent experiments and presented as means±SE.

Figure 6A:
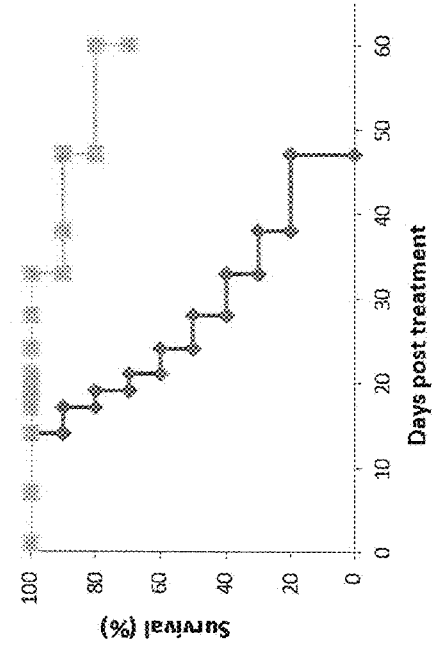
Figure 6B:
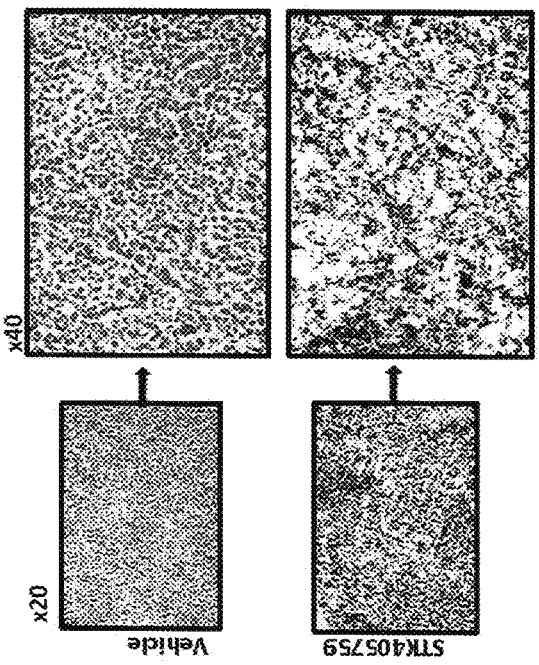
Figure 6C:
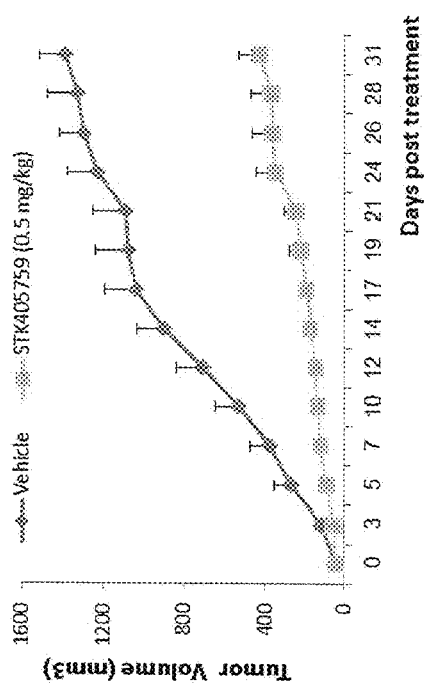
Figure 6D:
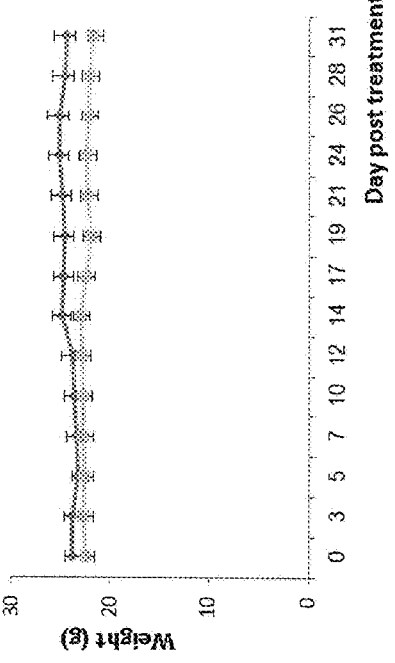

FIGS. 6A-D show that STK405759 induces inhibition of tumor growth in MM xenograft murine model. RPMIS cells ($7 \times 10^6$ mouse in 100 µl of PBS) were injected subcutaneously in SCID mice. Mice (n=10 per group) received STK405759 (0.5 mg/kg in 0.1 ml PBS) or control vehicle (0.1 ml PBS), by intraperitoneal (i.p.) administration once a day for 5 days. FIG. 6A—Tumor diameters were measured every 2-3 days with caliper, and tumor volumes were calculated using the formula of the volume of an ellipse: ½ (length×width$^2$). STK405759 significantly inhibited tumor growth (P<0.0005, t test). FIG. 6B—Kaplan-Meier analysis of overall survival confirmed that STK405759 increased survival compared with control mice. FIG. 6C—The weights of treated mice did not significantly change over the course of treatment with STK405759. FIG. 6D—Induction of apoptosis and cell death in tumors excised from vehicle or STK405759 (0.5 mg/kg) treated animals are shown by TUNEL assay. Photomicrographs show apoptotic cells (brown) using light microscopy (×20 and ×40 magnification).

DESCRIPTION OF SPECIFIC EMBODIMENTS OF THE INVENTION

The present invention, in some embodiments thereof, relates to compositions and methods for treating hematological malignancies.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Hematological malignancies are a distinct group of cancers, which are derived from cells originating from blood cells and bone marrow cells as well as immune cells within lymph nodes. The more prevalent cancers of this type include acute myeloid leukemia (AML), chronic myeloid leukemia (CML), acute lymphatic leukemia (ALL), chronic lymphatic leukemia (CLL). Hodgkin's disease and Non-Hodgkin lymphoma as well as multiple myeloma and myelodysplastic syndrome (MDS). Myeloproliferative diseases are related diseases. While there are treatment options for some of these diseases, further therapeutic approaches are urgently needed.

Whilst searching for a novel treatment modality for hematological malignancies, the present inventors have tested small molecules represented by Formula I, below, and specifically, STK405759, as potentially novel drugs for the treatment of hematological malignancies such as multiple myeloma (MM).

Figure 3C:
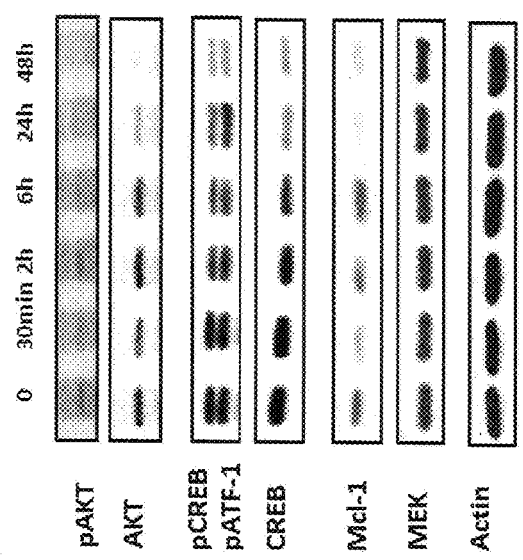

As is described hereinbelow and in the Examples section which follows, STK405759 had a potent cytotoxic activity against MM cell lines and primary patient-derived MM cells (FIGS. 1A-E and FIGS. 4A-C), regardless of their sensitivity to chemotherapy (FIGS. 5A-C). Importantly, the STK405759 was not cytotoxic to peripheral blood mononuclear cells (FIG. 1E). STK405759 suppressed proliferation of myeloma cells alone and when co-cultured with bone marrow stromal cells (FIGS. 2A-D). Similarly, STK405759 treatment of MM cells triggered G2 cell cycle arrest and induced apoptosis associated with the induction of caspase-8 and poly (ADP-ribose) polymerase cleavage (FIGS. 3A-D and 4A-C). STK405759 also decreased AKT and CREB protein expression in MM cell lines (FIGS. 3C-D). Combination studies of STK405759 with bortezomib, lenalidomide or dexamethasone showed significant synergistic cytotoxicity in MM cells (RPMIS and MM.1S (FIGS. 5A-C)). In vivo studies revealed decreased MM cell growth and prolonged survival of STK405759-treated mice as compared with controls. Importantly, analysis of excised tumors from treated animals confirmed apoptosis (FIGS. 6A-D).

Altogether, the present results place the compounds of the present invention as a pivotal treatment for hematological malignancies such as multiple myeloma.

Thus, according to an aspect of the invention there is provided a compound represented by Formula I:

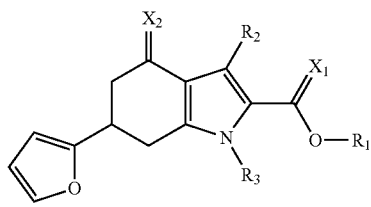

Formula I wherein:

$X_1$ and $X_2$ are each independently oxygen or sulfur;

$R_2$ and $R_3$ are each independently hydrogen or alkyl; and $R_1$ is alkyl, for use in the treatment of a hematological malignancy in a subject in need thereof.

According to an alternative or an additional aspect there is provided a use of a compound represented by Formula I:

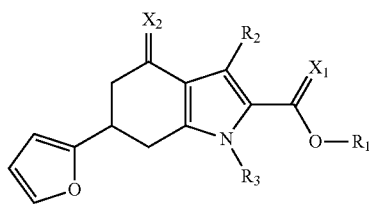

Formula I wherein:

$X_1$ and $X_2$ are each independently oxygen or sulfur;

$R_2$ and $R_3$ are each independently hydrogen or alkyl; and $R_1$ is alkyl, in the manufacture of a medicament identified for the treatment of a hematological malignancy.

According to yet an alternative or an additional aspect, there is provided a method of treating a hematological malignancy in a subject in need thereof, the method comprising administering to the subject a therapeutically effective amount of a compound represented by Formula I:

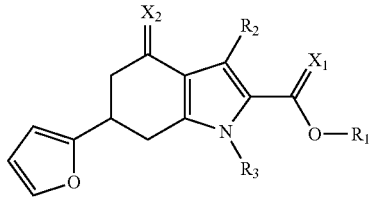

Formula I wherein:

$X_1$ and $X_2$ are each independently oxygen or sulfur;

$R_2$ and $R_3$ are each independently hydrogen or alkyl; and $R_1$ is alkyl, thereby treating the hematological malignancy.

According to still an alternative or an additional aspect there is provided an article of manufacture identified for the treatment of a hematological malignancy, comprising as active ingredients a compound represented by Formula I:

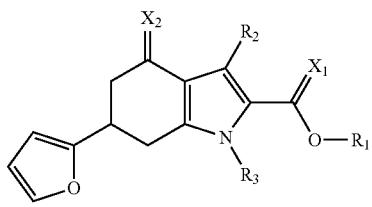

Formula I wherein:

$X_1$ and $X_2$ are each independently oxygen or sulfur;

$R_2$ and $R_3$ are each independently hydrogen or alkyl; and $R_1$ is alkyl, and a chemotherapy.

According to a further alternative or an additional aspect there is provided a pharmaceutical composition comprising as an active ingredient a compound represented by Formula I:

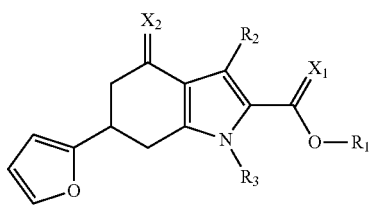

Formula I wherein:

$X_1$ and $X_2$ are each independently oxygen or sulfur;

$R_2$ and $R_3$ are each independently hydrogen or alkyl; and $R_1$ is alkyl, and a pharmaceutically acceptable carrier or diluents.

According to any one of the present embodiments, and any combination thereof, in formula I, substituents not shown in the structure are to be regarded as hydrogen substituents. It is to be noted, however, that any other substituents at these positions, for example, alkyls, cycloalkyls, heteroalicyclic, halo, nitro, cyano, and the like, including any one of the substituents described herein for alkyl or heteroaryl, for example, are also contemplated.

Further according to any one of the present embodiments, and any combination thereof, a compound represented by Formula I as described herein has an oxo/thiooxo-tetrahydroindole substituted by a furan as a skeleton. It is to be noted that compounds in which the furan moiety is replaced by other heteroaryl moiety, as described herein, are also contemplated. Also contemplated are compounds in which a substituent in one or more positions of the furan skeleton is other than hydrogen, as described herein.

In some of any of the embodiments described herein, and any combination thereof, one or both of $X_1$ and $X_2$ is oxygen. In some embodiments, $X_1$ is oxygen and $X_2$ is sulfur. In some embodiments, $X_1$ is sulfur and $X_2$ is oxygen. In preferred embodiments, both $X_1$ and $X_2$ are oxygen.

In some of any of the embodiments described herein, and any combination thereof, the oxo-tetrahydroindole skeleton is substituted at position 3 thereof by an alkyl, as defined herein, such that $R_2$ in Formula I is alkyl. In some embodiments, the alkyl is a lower alkyl, having 1-6 or 1-4 carbon atoms, and in some embodiments, it is methyl.

In some of any of the embodiments described herein, and any combination thereof, the nitrogen within the tetrahydroindole skeleton is a secondary amine, such that $R_3$ is hydrogen. Alternatively, $R_3$ can be an alkyl, preferably a lower alkyl, as defined herein.

It is to be noted that acid addition salts of the compounds represented by Formula I, as described herein in any one of the respective embodiments, are also contemplated, as is described in further detail hereinafter.

In a compound represented by Formula I as described herein, the oxo tetraindole skeleton is further substituted by a carboxylate or thiocarboxylate group, as depicted in Formula I. The carboxylate or thiocarboxylate may include an alkyl moiety as is in Formula I. In some embodiments, the alkyl has at least 2 carbon atoms. In some embodiments, the alkyl has at least 3 carbon atoms. In some embodiments, the alkyl has at least 4 carbon atoms, at least 5 carbon atoms, at least 6 carbon atoms, at least 7 carbon atoms, at least 8 carbon atoms, at least 9 carbon atoms or at least 10 carbon atoms. In some embodiments, the alkyl has from 2 to 10 carbon atoms, although higher alkyls are also contemplated.

In some of any one of the embodiments described herein, and any combination thereof, in Formula I as described herein: $X_1$ and $X_2$ are both oxygen; $R_2$ is alkyl, such as methyl; $R_3$ is hydrogen; and $R_1$ is a C5 alkyl (a linear alkyl being 5 carbon atoms in length; pentyl).

In some of any one of the embodiments described herein, and any combination thereof, an exemplary compound represented by Formula I is 6-(furan-2-yl)-3-methyl-4-oxo-1,5,6,7-tetrahydroindole-2-carboxylate (also termed STK405759), having the following structure:

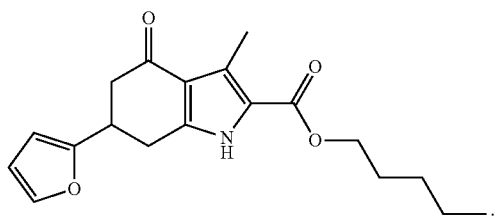 [SMILES: CCCCCOC(=O)c1[nH]c2c(c1C)C(=O)CC(c1ccco1)C2]

Herein throughout, the term "alkyl" describes a saturated aliphatic hydrocarbon, including straight chain and branched chain hydrocarbons. The alkyl can be of 1 to 40 carbon atoms, or of a to 20 carbon atoms in total or in length. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. In some embodiments, the alkyl is a medium size alkyl having 1 to 10 carbon atoms or 2 to 10 carbon atoms. In some embodiments, the alkyl is a lower alkyl having 1 to 6 or 1 to 4 carbon atoms. The alkyl group may be substituted or unsubstituted. Substituted alkyl may have one or more substituents, whereby each substituent group can independently be, for example, hydroxyl, thiol, hydroxyalkyl, trihaloalkyl, cycloalkyl, alkenyl, alkynyl, aryl, heteroaryl, heteroalicyclic, amine, halide, alkoxy, aryloxy, thioalkoxy, thioaryloxy, cyano, and nitro.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted. Substituted cycloalkyl may have one or more substituents, whereby each substituent group can independently be, for example, hydroxyl, thiol, hydroxyalkyl, trihaloalkyl, cycloalkyl, alkenyl, alkynyl, aryl, heteroaryl, heteroalicyclic, amine, halide, alkoxy, aryloxy, thioalkoxy, thioaryloxy, cyano, and nitro.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. Substituted heteroalicyclic may have one or more substituents, whereby each substituent group can independently be, for example, hydroxyl, thiol, hydroxyalkyl, trihaloalkyl, cycloalkyl, alkenyl, alkynyl, aryl, heteroaryl, heteroalicyclic, amine, halide, alkoxy, aryloxy, thioalkoxy, thioaryloxy, cyano, and nitro. Representative examples are piperidine, piperazine, tetrahydrofurane, tetrahydropyrane, morpholino and the like.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted. Substituted aryl may have one or more substituents, whereby each substituent group can independently be, for example, hydroxyl, thiol, hydroxyalkyl, trihaloalkyl, cycloalkyl, alkenyl, alkynyl, aryl, heteroaryl, heteroalicyclic, amine, halide, alkoxy, aryloxy, thioalkoxy, thioaryloxy, cyano, and nitro.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. Substituted heteroaryl may have one or more substituents, whereby each substituent group can independently be, for example, hydroxyl, thiol, hydroxyalkyl, trihaloalkyl, cycloalkyl, alkenyl, alkynyl, aryl, heteroaryl, heteroalicyclic, amine, halide, alkoxy, aryloxy, thioalkoxy, thioaryloxy, cyano, and nitro.

The term "halide" and "halo" describes fluorine, chlorine, bromine or iodine substituent.

The term "haloalkyl" describes an alkyl group as defined above, further substituted by one or more halide.

The term "hydroxy" describes a —OH group.

The term "alkoxy" describes both an —O-alkyl and an —O-cycloalkyl group, as defined herein.

The term "aryloxy" describes both an —O-aryl and an —O-heteroaryl group, as defined herein.

The term "thiohydroxy" or "thiol" describes a —SH group.

The term "thioalkoxy" describes both a —S-alkyl group, and a —S-cycloalkyl group, as defined herein.

The term "thioaryloxy" describes both a —S-aryl and a —S-heteroaryl group, as defined herein.

The term "cyano" describes a —C≡N group.

The term "nitro" describes an —NO$_2$ group.

Each of the compounds described herein can be utilized in its free base form or as a pharmaceutically acceptable salt.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound.

In the case of compounds represented by Formula I as described herein, a pharmaceutically acceptable salt can be an acid addition salt comprising at least one basic (e.g., amine) group of the compound which is in a positively charged form (e.g., an ammonium ion), in combination with at least one counter-ion, derived from the selected acid, that forms a pharmaceutically acceptable salt.

The acid addition salts of the compounds described herein may therefore be complexes formed between one or more amino groups of the compound of Formula I and one or more equivalents of an acid.

The acid addition salts may include a variety of organic and inorganic acids, such as, but not limited to, hydrochloric acid which affords a hydrochloric acid addition salt, hydrobromic acid which affords a hydrobromic acid addition salt, acetic acid which affords an acetic acid addition salt, ascorbic acid which affords an ascorbic acid addition salt, benzenesulfonic acid which affords a besylate addition salt, camphorsulfonic acid which affords a camphorsulfonic acid addition salt, citric acid which affords a citric acid addition salt, maleic acid which affords a maleic acid addition salt, malic acid which affords a malic acid addition salt, methanesulfonic acid which affords a methanesulfonic acid (mesylate) addition salt, naphthalenesulfonic acid which affords a naphthalenesulfonic acid addition salt, oxalic acid which affords an oxalic acid addition salt, phosphoric acid which affords a phosphoric acid addition salt, toluenesulfonic acid which affords a p-toluenesulfonic acid addition salt, succinic acid which affords a succinic acid addition salt, sulfuric acid which affords a sulfuric acid addition salt, tartaric acid which affords a tartaric acid addition salt and trifluoroacetic acid which affords a trifluoroacetic acid addition salt.

The compounds described herein may possess asymmetric carbon atoms (optical centers) or double bonds; the racemates, diastereomers, geometric isomers and individual isomers are encompassed within the scope of the present invention.

As used herein, the term "enantiomer" describes a stereoisomer of a compound that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems.

The compounds described herein can exist in unsolvated forms as well as solvated forms, including hydrated forms. In general, the solvated forms are equivalent to unsolvated forms and are encompassed within the scope of the present invention.

The term "solvate" refers to a complex of variable stoichiometry (e.g., di-, tri-, tetra-, penta-, hexa-, and so on), which is formed by a solute (the conjugate described herein) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

Certain compounds of the present invention may exist in multiple crystalline or amorphous forms. In general, all physical forms are equivalent for the uses contemplated by the present embodiments and are intended to be within the scope of the present invention.

According to a specific embodiment, the compound induces apoptosis of multiple myeloma cells optionally associated with the induction of caspase-8 and poly (ADP-ribose) polymerase cleavage. Methods of detecting apoptosis are well known in the art and include but are not limited to caspase activation e.g., by substrate cleavage e.g., PARP and M30; membrane alteration e.g., Annexin V binding; DNA fragmentation e.g., TUNEL, BrdU; or mitochondrial damage.

According to an alternative or an additional embodiment, the compound does not affect (e.g., less than 10%) peripheral blood mononuclear cells (as shown in Example 1), as assayed e.g., by cell viability/proliferation assay e.g., XTT.

According to an alternative or an additional embodiment, the compound elicits G2 cell cycle arrest, as may be assayed by FACS, see FIG. 4A.

According to an alternative or an additional embodiment, the compound down-regulates AKT and/or CREB protein expression, as may be assayed by Western blotting (see e.g., FIGS. 3C and 3D).

As used herein "a subject in need thereof" refers to a subject who has been diagnosed with a hematological malignancy, e.g., multiple myeloma. The subject may be a mammal (e.g., human being), of any gender or age.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

As used herein the phrase "hematological malignancies" refer to any cancer that originates in the cells of blood-forming tissue, such as the bone marrow, or in the cells of the immune system.

The hematological malignancy can be leukemia or lymphoma. In the context of the invention, the hematological malignancy may be acute myeloid leukemia (AML), chronic myeloid leukemia (CML), acute lymphatic leukemia (ALL), chronic lymphatic leukemia (CLL), Hodgkin's disease, Non-Hodgkin lymphoma, multiple myeloma, myelodysplastic syndrome (MDS) or myeloproliferative diseases. According to a specific embodiment, the hematological malignancy is a myeloid malignancy that originates from malignant hematopoietic myeloid progenitor cells in the bone marrow, such as the precursor cells of red cells, platelets and granulocytes, e.g., essential thrombocythemia (ET), polycythemia vera (PV) and myelofibrosis (MF).

According to a specific embodiment, the hematological malignancy does not form solid tumors.

According to a specific embodiment, the hematological malignancy is multiple myeloma.

According to a specific embodiment, the hematological malignancy is not ALL.

According to a specific embodiment, the hematological malignancy is characterized by over-expression and/or over activation of cyclic-AMP responsive element-binding protein (CREB).

As used herein over-expression and/or over activation of CREB refers to at least 10%, 20%, 30%, 40%, 50%, or more say 60%, 70%, 80% or higher activity or expression of B+CREB as compared to same in a normal tissue/cells or the same origin and developmental stage.

CREB, e.g., CREB1_HUMAN P16220, is a cellular transcription factor. It binds to certain DNA sequences called cAMP response elements (CRE), thereby increasing or decreasing the transcription of the downstream genes. CREB activation is funneled by a plurality of pathways including receptor tyrosine kinases (e.g., via Akt), G-protein coupled receptors and calcium.

Methods of analyzing CREB activity or expression are well known in the art, some are described in the Examples section which follows e.g., Western blotting, and transcription factor activity assay.

Subjects who are suspected of having a hematological malignancy may be diagnosed using methods which are well known in the ar. A complete blood count and blood film are essential, as malignant cells can show in characteristic ways on light microscopy. When there is lymphadenopathy, a biopsy from a lymph node is generally undertaken surgically. In general, a bone marrow biopsy is part of the "work up" for the analysis of these diseases. All specimens are examined microscopically to determine the nature of the malignancy. A number of these diseases can now be classified by cytogenetics (AML, CML) or immunophenotyping (lymphoma, MM, CLL) of the malignant cells.

According to a specific embodiment, the tumor (subject) may exhibit resistance to therapy e.g., chemotherapy.

As used herein "resistance" refers to non-responsiveness to anti-cancer treatment as may be manifested by tumor load, in-vitro activity assays and/or patient survival.

According to a specific embodiment, resistance refers to no amelioration in disease symptoms or progression according to a regulatory agency guidelines (e.g., FDA) for the specific anti-cancer therapy, e.g., chemotherapy, used. Resistance to treatment can be primary resistance or acquired resistance.

According to specific embodiments the resistance is an acquired resistance.

As used herein the term "acquired resistance" refers to progression of resistance following initial positive response to therapy.

According to a specific embodiment the cancer is MM which exhibits chemoresistance such as to bortezomib (BTZ), lenalidomide (LEN) and dexamethasone (DEX).

As shown in Example 5 of the Examples section which follows, treatment of MM with STK405759 and standardly used chemotherapy, resulted in a synergistic effect as shown in FIGS. 5A-C. Hence, combinations of novel and/or conventional anti-cancer agents may achieve higher clinical response rates than a single agent(s).

Thus according to a specific embodiment, there is provided use of the compound of the present invention e.g., STK405759, together with a suitable chemotherapy for the treatment of hematological malignancies.

According to a specific embodiment, the anti-cancer agent (e.g., chemotherapy, immunotherapy, radiotherapy) is administered concomitantly with the compound of the invention.

According to a specific embodiment, the anti-cancer agent (e.g., chemotherapy, immunotherapy, radiotherapy) is administered following administration of the compound of the invention.

According to a specific embodiment, the administration of the compound of the invention may facilitate in reducing standard doses of respective anti-cancer therapy, thereby avoiding sytotoxic effects. Thus, according to some embodiments of the invention, the antibiotic may be administered in an amount which is at least 20% or 30% (e.g., 20-30%, 20-40%, 20-60%) lower than in standard use for the respective indication.

According to a specific embodiment, the anti-cancer agent (e.g., chemotherapy, immunotherapy, radiotherapy) is administered prior to administration of the compound of the invention.

Accordingly, there is provided an article of manufacture identified for the treatment of a hematological malignancy, comprising as active ingredients a compound represented by Formula I:

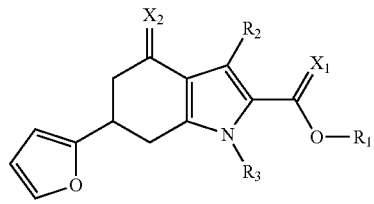

Formula I wherein:
$X_1$ and $X_2$ are each independently oxygen or sulfur;
$R_2$ and $R_3$ are each independently hydrogen or alkyl; and
$R_1$ is alkyl,
and a chemotherapy.

According to a specific embodiment the compound and the anti-cancer therapy e.g., chemotherapy, are in a co-formulation, such as in a single container.

According to a specific embodiment the compound and the anti-cancer therapy e.g., chemotherapy, are in separate formulations i.e., separate containers.

Further description of articles and kits is provided hereinbelow.

The compound and optionally anti-cancer therapy of some embodiments of the invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the compound and optionally anti-cancer therapy accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant. e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form. e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle. e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

In some embodiments, where the compound is mixed with carriers and/or excipients, the concentration of the compound in the pharmaceutical composition can range from 0.01 mg/ml to 1 mg/ml, e.g., 0.01 mg/ml to 0.5 mg/ml, 0.01 mg/ml to 0.2 mg/ml, 0.05 mg/ml to 1 mg/ml, 0.05 mg/ml to 0.5 mg/ml, 0.1 mg/ml to 0.5 mg/ml.

In some embodiments, when a concentration of the compound in a pharmaceutical composition is limited by, for example, the solubility of the compound in the carrier, various techniques can be employed in order to increase the concentration of the compound in the formulation. These include, for example, addition of solubilizers, surfactants, hydrating agents, and other additives, as known in the art, and/or formulating the compound in the presence of micelles.

Pharmaceutical compositions suitable for use in context of some embodiments of the invention include compositions wherein the active ingredients are contained in an amount effective to achieve the intended purpose. More specifically, a therapeutically effective amount means an amount of active ingredients (compound and optionally anti-cancer therapy) effective to prevent, alleviate or ameliorate symptoms of a disorder (e.g., hematological malignancy e.g., MM) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit or article of manufacture, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

As used herein the term "about" refers to ±10%

The terms "comprises", "comprising", "includes". "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5.000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal. "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols, 1-4. Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press. (1986); "A Practical Guide to Molecular Cloning" Perbal. B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Materials and Methods

Cell Lines—

The following panel of human multiple myeloma (MM) cell lines was used: RPMI-S (ATCC® CCL-155), RPMI-LR5, RPMI-MR20, MM.1S (ATCC® CRL-2974). OPM1, OPM-2, U266 ATCC® TIB-196 and CAG. The human immortalized bone marrow stromal cell (BMSC) line HS-5 was obtained from ATCC® CRL-11882. MM cell lines were grown in RPMI and HS-5 in DMEM, supplemented with 10% fetal calf serum, 2 mM L-glutamine, 100 units/mL penicillin and 100 µg/mL streptomycin (Biological Industries, Beit Haemek, Israel), and incubated in a humidified atmosphere of 5% $CO_2$ and 95% air at 37° C.

Compounds and Reagents—

STK405759 (C19H23NO4, molecular weight 329.390) was synthesized and provided by M Vitas lab. Melphalan, Dexamethasone and Doxorubicin were purchased from Sigma-Aldrich. Lenalidomide and Bortezomib were purchased from Selleckchem.

Cell Viability Assay—

MM cell lines were plated at a density of $2\times10^4$ cells per well in 96-wells and treated with different concentrations of STK405759. For patient samples, bone marrow aspirates from MM patients were collected, mononuclear cells were separated by Ficoll density gradient centrifugation and myeloma cells selected using CD138 microbeads (Miltenyi Biotec). Purified CD138$^+$ cells from patients were plated at a density of $2\times10^4$ cells per well and treated for 48 h with different concentrations of STK405759. Peripheral blood samples were processed by Ficoll density gradient centrifugation to isolate peripheral blood mononuclear cells (PBMCs). PBMCs were plated at $2\times10^4$ cells per well and exposed to different concentrations of STK405759 for 48 h. Cell viability was measured using XTT cell proliferation Kit (Biological Industries) according to manufacture instructions.

Apoptosis Analysis by FACS—

RPMI-S cells were treated with 40 and 70 nmol/l STK405759 for 0 (control), 24 and 48 h. For evaluation of apoptosis, cells were processed using an Annexin V/propidium iodide (PI) kit (Becton Dickinson Biosciences) according to manufacturer's instructions.

Cell-Cycle Analysis—

RPMIS cells were exposed to 70 nmol/l STK405759 for different time periods, permeabilized by 70% ethanol at −20° C. overnight and incubated with 50 μg/ml PI and 20 units/ml RNase-A (Roche Diagnostics). DNA content was analyzed by flow cytometry. Data were collected using FACSCalibur (Becton Dickinson) and analyzed with the CellQuest software.

Immunoblotting Analysis—

For immunoblotting analyses, MM cell lines were cultured in the presence of STK405759 (40 and 70 nmol/L), which was added for 30 minutes, 2, 6, 24 and 48 h (untreated=control). Cells were lysed in RIPA-lysis buffer containing 10 mM sodium pyrophosphate, 2 mM sodium orthovanadate, 5 mM sodium fluoride, 5 g/mL aprotinin, 5 g/mL leupeptin, and 1 mM phenylmethylsulfonyl fluoride. Proteins were separated by sodium dodecyl sulfate-polyacrylamide gel electrophoresis, transferred onto nitrocellulose membranes and immunoblotted with anti-pAKT (Ser473), AKT, pCREB (Ser133)/pATF1(Ser63). CREB. MEK, Mcl-1, caspase-3, caspase-8, caspase-9, poly ADP ribose polymerase (PARP) (Cell Signaling Technology) and actin antibodies (Santa Cruz Biotechnology). Immunoreactive bands were detected by Western Blot chemiluminescence reagents (Thermo Scientific) and exposed on Kodak-XAR film.

Xenograft Murine Model—

Male SCID mice (6-8 week old) were maintained in accordance with Institutional Animal Care Use Committee guidelines. Mice were housed in the Animal Research Facility of Chaim Sheba Medical Center, Israel, and experiments were performed in accordance to approved protocols. During the experiment, the mice were gamma-irradiated (150 rads) using Cs137 γ-irradiator source and 24 h post-irradiation injected subcutaneously with $7 \times 10^6$ RPMIS MM cells suspended in PBS. Two weeks later, when tumors reached 40-70 mm$^3$, mice were randomly divided into two groups (10 mice/group), and the following treatment protocol was implemented: Group 1: control (0.05 ml DMSO) administered intraperitoneally (i.p.) for 5 days a week throughout the duration of experiment.

Group 2: STK405759 (0.5 mg/kg in 0.05 ml DMSO) administered i.p. for 5 days a week throughout the duration of experiment.

Mice were monitored every 2-3 d for changes in body weight and tumor burden. Tumor volumes were measured by a caliper every alternate day and calculated using the following formula: length×width$^2$×0.5. Mice were sacrificed in accordance with institutional guidelines when tumors reached 1.5 cm$^3$ or if the mice appeared moribund, to prevent unnecessary morbidity to the mice. Following sacrifice, tumors were immediately collected and evaluated for induction of apoptosis and cell death by TdT-mediated dUTP nick end labeling (TUNEL) assay.

Example 2

STK405759 Reduces Viability of MM Cells Regardless of their Sensitivity to Conventional Chemotherapy To monitor the effect of STK405759 on MM, the compound was incubated in the presence of various MM cell lines. STK405759 significantly decreased survival of several human MM cells in a concentration- and time-dependent manner, including those MM cell lines resistant to currently in use anti-MM agents like RPMI-MR20 (mitoxantrone-resistant cells) and RPMI-LR5 (LEN-resistant cells) (FIGS. 1B-C). The IC50 value was lower than 44 nM for each cell line.

To determine the effect of STK405759 on primary MM cells, affinity-purified CD138+ cells from bone marrow samples of 2 MM patients were treated for 48 h with different concentrations of STK405759.

As shown in FIG. 1D, a dose-dependent cytotoxic response was observed. Likewise, PBMC from the same patients and from healthy donors (FIGS. 1D-E) were non responsive to the cytotoxic effect of STK405759. Thus, STK405759 has a potent and selective cytotoxic effect against myeloma cells.

Since BMSC trigger and maintain MM cell homing, proliferation, and drug resistance [13-15], the present inventors have assessed whether MM cell sensitivity to STK405759 is attenuated by co-culture with bone marrow stromal cells. In order to quantify viability of MM cells cultured alone or co-cultured with HS-5 bone marrow stromal cells. MM cells were stained with CFSE. The cells were cultured with increasing concentrations of STK405759 in the presence or absence of HS-5 for 48 h and stained using propidium iodide (PI) to distinguish viable from nonviable cells.

As shown in FIG. 2A, unlabeled-HS-5 stromal cells were unaffected by STK405759 treatment. However, the viability of RPMIS cells decreased by STK405759 treatment (CFSE+/PI+) at a concentration-dependent manner when the cells were cultured alone and in the presence of stromal cells (FIG. 2B).

It has been demonstrated that IL-6 and IGF-1 induce both growth and inhibition of apoptosis in MM cells [15-17] therefore, the ability of STK405759 to suppress the exogenous IL-6 and IGF-1 induced proliferation and survival of myeloma cells was tested. The cytokines did not cause a significant shift in IC50 for RPMIS cells and did not protect them from STK405759-mediated inhibition of survival.

Example 3

STK405759 Induces Apoptosis and Inhibits Proliferation of MM Cells

STK405759 treatment increased apoptotic cell death of MM cells (Annexin V−/PI+ and Annexin V+/PI+) at a time- and concentration-dependent manner (FIG. 3A). The induction of apoptosis was supported by the cleavage of caspase-8 and PARP proteins in MM treated cells (FIG. 3B) and decrease in myeloid cell leukaemia-1 (Mcl-1) protein level (FIG. 3C), that initiated apoptosis in MM cells [18, 19].

Additionally, the induction of apoptosis was supported by the increase of subG0/G1 phase peak by nuclear PI DNA staining in STK405759 treated cells (FIGS. 4A-B). PI DNA staining also showed that STK405759 induced a pronounced $G_2/M$ phase arrest of RPMIS cells as early as 3 h of treatment (FIGS. 4A-B). In order to quantify proliferation. MM cells were stained with CFSE and counterstained with PI to distinguish live from non-viable cells. There was an inverse correlation between CFSE-staining intensity and number of cell divisions. As shown in FIG. 4C, STK405759 decreased cell proliferation of RPMIS cells at 48 h of treatment in a concentration dependent manner (FIG. 4C).

Example 4

Effect of STK405759 on Cell Signalling

In order to understand the impact of STK405759 on intracellular pathways, changes in expression of signaling related-proteins were evaluated. STK4057569 decreased the expression level of pAKT, AKT, pCREB/pATF1, CREB and Mcl-1 proteins in RPMIS treated cells (FIG. 3C). Since CREB supports multiple signaling pathways that are often deregulated in cancer cells, it constitutes an attractive therapeutic target for MM. Therefore, the present inventors next evaluated changes in CREB expression as a result of STK405759 treatment in human MM cell lines. STK405759 decreased CREB expression in each of the MM cell lines tested in a dose and time dependent manner (FIG. 3D). Since Mcl-1 is known to be a direct target of CREB [18, 19], the decrease in Mcl-1 expression (FIG. 3C), could be directly associated to the decrease in activity of CREB transcription factor.

Example 5

STK405759 Enhance Cytotoxicity of Conventional and Novel Anti-MM Therapies

The present data shows that STK405759 has a potent and selective anti-MM activity. Combinations of novel and/or conventional anti-MM agents may achieve higher clinical response rates than a single agent(s). Therefore, the response of RPMIS and MM.1S cells to STK405759 treatment in combination with currently in use anti-MM agents (bortezomib (BTZ), lenalidomide (LEN), dexamethasone (DEX), melphalan (MEL) and doxorubicin (DOXO) was evaluated. The anti-MM activity of combined treatment was analysed by XTT assays, and the presence of synergistic cytotoxic effects was evaluated using the Chou-Talalay method based on the median-effect equation and the classic isobologram equation [22] and compusyn computer software [23].

The fractions affected and the combination indices for each of the combinations are summarized in FIGS. 5A-C and Table 1 below. Analysis with the CompuSyn software indicates that STK405759 triggered a synergistic effect when combined with LEN, DEX or BTZ (combination index CI<1). Even when survival of MM cells decreased after co-treatment of STK405759 with MEL or DOXO, according to the Chou-Talalay method they had an antagonist cytotoxic effect (combination index CI>1). These results provide the framework for evaluation of STK405759 in combination with LEN, DEX and BTZ for future clinical studies.

Table 1—STK405759 Enhances the Effect of Anti-MM Agents

RPMI and MM.1S cells were cultured for 48 hours with STK405759 (45 nM), in combination with DEX (1 and 5 nM), LEN (5 and 25 μM), BTZ (1 and 5 nM), melphalan (2.5 and 5 μM) and doxorubicin (10 and 30 nM). CI value <1, =1, >1 indicates synergism, additive effect, and antagonism, respectively, (n=3 independent experiments). The CI values were calculated by the Chou-Talalay method based on the median-effect equation and the classic isobologram equation [22], using compusyn computer software [23].

|  | | STK405759 45 nM | |
|---|---|---|---|
| Combination Index | | MM.1S | RPMIS |
| BTZ (nM) | 1 | 0.62 ± 0.14 | 0.88 ± 0.02 |
|  | 5 | 0.58 ± 0.02 | 0.78 ± 0.08 |
| LEN (μM) | 5 | 0.62 ± 0.09 | 0.77 ± 0.09 |
|  | 25 | 0.58 ± 0.09 | 0.74 ± 0.05 |
| DEX (nM) | 1 | 0.76 ± 0.15 | 0.76 ± 0.06 |
|  | 5 | 0.63 ± 0.09 | 0.84 ± 0.03 |
| MEL (μM) | 2.5 | 1.50 ± 0.10 | 1.08 ± 0.09 |
|  | 5 | 1.42 ± 0.06 | 1.14 ± 0.05 |
| DOXO (nM) | 10 | 1.30 ± 0.06 | 1.44 ± 0.01 |
|  | 30 | 1.54 ± 0.08 | 1.63 ± 0.10 |

Example 6

In Vivo Activity of STK405759

STK405759 treatment significantly inhibited tumor growth compared to control mice (FIG. 6A). Statistically significant changes in tumor volume were observed on day 7 of treatment (P<0.05, t test), until the end of the experiment (P<0.00005, t test). STK405759 increased significantly the overall survival of treated mice; whereas control mice had median overall survival of 28 days, STK405759 treated mice didn't reach the median overall survival after a follow-up of 60 days (FIG. 6B). No significant changes in weight or other signs of potential toxicity were observed during treatment with STK405759 (FIG. 6C). Sections from tumors were stained for terminal uridine deoxynucleotidyl transferase dUTP nick-end labeling (TUNEL) for detecting DNA fragmentation that results from apoptotic signaling cascades in the cells. STK405759 increased apoptosis in the tumors of treated mice (FIG. 6D), confirming the previously in vitro results, described above.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

References (Other References are Cited Throughout)

[1]. American Cancer Society. How many people get multiple myeloma?; 2013, www(dot)cancer(dot)org/cancer/multiplemyeloma/overviewguide/multiplemyelomaoverview-key-statistics.

[2]. Avet-Loiseau H, Attal M, Moreau P, Charbonnel C, Garban F. Hulin C. Leyvraz S, Michallet M, Yakoub-Agha I. Garderet L et al: Genetic abnormalities and survival in multiple myeloma: the experience of the Intergroupe Francophone du Myelome. *Blood* 2007, 109 (8):3489-3495.

[3]. [Waxman A J. Mink P J, Devesa S S, Anderson W F, Weiss B M, Kristinsson S Y, et al. Racial disparities in incidence and outcome in multiple myeloma: a population-based study. Blood 2010; 116(25):5501-6. December 16.
[4]. Sant M, Allemani C. Tereanu C, De Angelis R, Capocaccia R, Visser O. HAEMACARE Working Group Incidence of hematologic malignancies in Europe by morphologic subtype: results of the HAEMACARE project. Blood 2010; 116 (November 34-3724:((19).
[5]. Kumar S K, Rajkumar S V, Dispenzieri A. Lacy M Q, Hayman S R, Buadi F K, Zeldenrust S R, Dingli D. Russell S J, Lust J A et al: Improved survival in multiple myeloma and the impact of novel therapies. *Blood* 2008, 111(5):2516-2520.
[6]. Rajkumar S V: Treatment of multiple myeloma. *Nature reviews Clinical oncology* 2011, 8(8):479-491.
[7]. Wang Y, Bolton E. Dracheva S, Karapetyan K. Shoemaker B A. Suzek T O, Wang J, Xiao J, Zhang J, Bryant S H: An overview of the PubChem BioAssay resource. Nucleic acids research 2010, 38(Database issue):D255-266.
[8]. Wang Y X J, Suzek T O, Zhang J, Wang J, Zhou Z, Han L, Karapetyan K, Dracheva S, Shoemaker B A. Bolton E, Gindulyte A, Bryant S H.: PubChem's BioAssay Database. Nucleic Acids Res 40(1):D400-12 2012 January; 40(1):D400-12.
[9]. Shaywitz A J, Greenberg M E: CREB: a stimulus-induced transcription factor activated by a diverse array of extracellular signals. Annual review of biochemistry 1999, 68:821-861.
[10]. Hsu J, Shi Y, Krajewski S, Renner S, Fisher M, Reed J C, Franke T F, Lichtenstein A: The AKT kinase is activated in multiple myeloma tumor cells. Blood 2001, 98(9):2853-2855.
[11]. Steinbrunn T, Stuhmer T, Gattenlohner S, Rosenwald A, Mottok A, Unzicker C, Einsele H, Chatterjee M, Bargou R C: Mutated RAS and constitutively activated Akt delineate distinct oncogenic pathways, which independently contribute to multiple myeloma cell survival. Blood 2011, 117(6):1998-2004.
[12]. De Vos J, Jourdan M, Tarte K, Jasmin C, Klein B: JAK2 tyrosine kinase inhibitor tyrphostin AG490 down-regulates the mitogen-activated protein kinase (MAPK) and signal transducer and activator of transcription (STAT) pathways and induces apoptosis in myeloma cells. British journal of haematology 2000, 109(4):823-828.
[13]. Yang J, He J, Wang J, Cao Y, Ling J, Qian J, Lu Y, Li H, Zheng Y, Lan Y et al: Constitutive activation of p38 MAPK in tumor cells contributes to osteolytic bone lesions in multiple myeloma. Leukemia 2012, 26(9): 2114-2123.
[14]. Zhang X, Odom D T, Koo S H, Conkright M D. Canettieri G, Best J, Chen H, Jenner R, Herbolsheimer E, Jacobsen E et al: Genome-wide analysis of cAMP-response element binding protein occupancy, phosphorylation, and target gene activation in human tissues. Proceedings of the National Academy of Sciences of the United States of America 2005, 102(12):4459-4464.
[15]. Lauta V M: A review of the cytokine network in multiple myeloma: diagnostic, prognostic, and therapeutic implications. *Cancer* 2003, 97(10):2440-2452.
[16]. Mitsiades CS1, McMillin D W, Klippel S, Hideshima T, Chauhan D, Richardson P G, Munshi N C, Anderson K C. The role of the bone marrow microenvironment in the pathophysiology of myeloma and its significance in the development of more effective therapies. Hematol Oncol Clin North Am. 2007 December; 21(6):1007-34.
[17]. Jourdan M, De Vos J. Mechti N, Klein Regulation of Bcl-2-family proteins in myeloma cells by three myeloma survival factors: interleukin-6, interferon-alpha and insulin-like growth factor 1 B. Cell Death Differ. 2000 December; 7(12):1244-52.
[18]. Chao J R, Wang J M, Lee S F, Peng H W, Lin Y H, Chou C H, Li J C, Huang H M, Chou C K, Kuo M L et al: mcl-1 is an immediate-early gene activated by the granulocytemacrophage colony-stimulating factor (GM-CSF) signaling pathway and is one component of the GM-CSF viability response. *Molecular and cellular biology* 1998, 18(8):4883-4898.
[19]. Fan F, Tonon G, Bashari M H, Vallet S, Antonini E, Goldschmidt H, Schulze-Bergkamen H, Opferman J T, Sattler M, Anderson K C et al: Targeting Mcl-1 for multiple myeloma (MM) therapy: Drug-induced generation of Mcl-1 fragment Mcl-1 triggers MM cell death via c-Jun upregulation. *Cancer letters* 2013.
[20]. Chou C H, Lai S L, Chen C N, Lee P H, Peng F C, Kuo M L, Lai H S: IL-6 regulates Mcl-1L expression through the JAK/PI3K/Akt/CREB signaling pathway in hepatocytes: implication of an anti-apoptotic role during liver .regeneration. PloS one 2013, 8(6):e66268
[21]. Wang J M, Chao J R, Chen W, Kuo M L, Yen J J, Yang-Yen H F: The antiapoptotic gene mcl-1 is up-regulated by the phosphatidylinositol 3-kinase/Akt signaling pathway through a transcription factor complex containing CREB. Molecular and cellular biology 1999, 19(9):6195-6206.
[22]. Chou T C, Talalay P: Quantitative analysis of dose-effect relationships: the combined effects of multiple drugs or enzyme inhibitors. *Advances in enzyme regulation* 1984, 22:27-55.
[23]. Chou T C: Theoretical basis, experimental design, and computerized simulation of synergism and antagonism in drug combination studies. *Pharmacological reviews* 2006, 58(3):621-681.
[24]. Tu Y, Gardner A, Lichtenstein A, The phosphatidylinositol 3-kinase/AKT kinase pathway in multiple myeloma plasma cells: roles in cytokine-dependent survival and proliferative responses. Cancer Research. 2000; 60(23):6763-6770.
[25]. Harvey R D, Lonial S. PI3 kinase/AKT pathway as a therapeutic target in multiple myeloma. Future Oncology. 2007; 3(6):639-647.
[26]. Keane N A, Glavey S V, Krawczyk J, O'Dwyer M: AKT as a therapeutic target in multiple myeloma. Expert opinion on therapeutic targets 2014, 18(8):897-915.
[27]. Park M H, Lee H S, Lee C S, You S T, Kim D J, Park B H, Kang M J, Heo W D, Shin E Y, Schwartz M A et al: p21-Activated kinase 4 promotes prostate cancer progression through CREB. Oncogene 2013, 32(19):2475-2482.
[28]. Garcia G E, Nicole A, Bhaskaran S, Gupta A, Kyprianou N, Kumar A P: Akt- and CREB-mediated prostate cancer cell proliferation inhibition by Nexrutine, a *Phellodendron amurense* extract. Neoplasia 2006, 8(6):523-533.
[29]. Fan C F, Mao X Y, Wang E H: Elevated p-CREB-2 (ser 245) expression is potentially associated with carcinogenesis and development of breast carcinoma. Molecular medicine reports 2012, 5(2):357-362.
[30]. Son J, Lee J H, Kim H N, Ha H, Lee Z H: cAMP-response-element-binding protein positively regulates breast cancer metastasis and subsequent bone destruction. Biochemical and biophysical research communications 2010, 398(2):309-314.

[31]. Seo H S, Liu D D, Bekele B N, Kim M K, Pisters K, Lippman S M, Wistuba, I I, Koo J S: Cyclic AMP response element-binding protein overexpression: a feature associated with negative prognosis in never smokers with non-small cell lung cancer. Cancer research 2008, 68(15):6065-6073.
[32]. Jean D, Harbison M, McConkey D J, Ronai Z, Bar-Eli M: CREB and its associated proteins act as survival factors for human melanoma cells. The Journal of biological chemistry 1998, 273(38):24884-24890.
[33]. Shankar D B, Cheng J C, Kinjo K, Federman N, Moore T B, Gill A, Rao N P, Landaw E M, Sakamoto K M: The role of CREB as a proto-oncogene in hematopoiesis and in acute myeloid leukemia. Cancer cell 2005, 7(4):351-362.
[34]. Shankar D B, Sakamoto K M: The role of cyclic-AMP binding protein (CREB) in leukemia cell proliferation and acute leukemias. Leukemia & lymphoma 2004, 45(2): 265-270.
[35]. Shankar D B, Cheng J C, Sakamoto K M: Role of cyclic AMP response element binding protein in human leukemias. Cancer 2005, 104(9):1819-1824.
[36]. Cheng J C, Esparza S, Sandoval S, Shankar D, Fu C, Sakamoto K M: Potential role of CREB as a prognostic marker in acute myeloid leukemia. Future oncology 2007, 3(4):475-480.
[37]. Fuhler G M, Diks S H, Peppelenbosch M P, Kerr W G: Widespread deregulation of phosphorylation-based signaling pathways in multiple myeloma cells: opportunities for therapeutic intervention. Molecular medicine 2011, 17(7-8):790-798.
[38]. Takii R, Fujimoto M, Tan K, Takaki E, Hayashida N, Nakato R, Shirahige K, Nakai A: ATF1 modulates the heat shock response by regulating the stress-inducible HSF1-transcription complex. Molecular and cellular biology 2014.
[39]. Liu Z, Li T, Jiang K, Huang Q, Chen Y, Qian F: Induction of chemoresistance by all-trans retinoic acid via a noncanonical signaling in multiple myeloma cells. PloS one 2014, 9(1):e85571.
[40]. Shao S, Huang X, Wang Y, He S, Xu X, Zhu X, Yang X, Ding Z, Yao L, Huang Y et al: A role for activator of G-protein signaling 3 (AGS3) in multiple myeloma. International journal of hematology 2014, 99(1):57-68.

What is claimed is:

1. A method of treating multiple myeloma or myelofibrosis in a subject in need thereof, the method comprising administering to the subject a therapeutically effective amount of a pentyl 6-(furan-2-yl)-3-methyl-4-oxo-1, 5, 6, 7-tetrahydroindole-2-carboxylate:

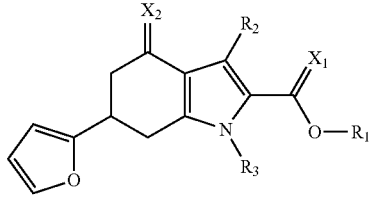

Formula I thereby treating the multiple myeloma or the myelofibrosis.

2. The method of claim 1, wherein said multiple myeloma or said myelofibrosis is characterized by overexpression and/or over-activation of cyclic-AMP response element-binding protein (CREB).

3. The method of claim 1, wherein said multiple myeloma or said myelofibrosis is characterized by chemoresistance.

4. The method of claim 3, wherein said chemoresistance is for a chemotherapy selected from the group consisting of bortezomib (BTZ), lenalidomide (LEN) and dexamethasone (DEX).

5. The method of claim 1, wherein said pentyl 6-(furan-2-yl)-3-methyl-4-oxo-1, 5, 6, 7-tetrahydroindole-2-carboxylate is provided as a pharmaceutical composition which further comprises a carrier.

6. The method of claim 1, comprising administering to said subject an anti-cancer agent.

7. The method of claim 6, wherein said anti-cancer agent is suitable for the treatment of multiple myeloma or myelofibrosis.

8. The method of claim 6, wherein said anti-cancer agent is selected from the group consisting of bortezomib (BTZ), lenalidomide (LEN) and dexamethasone (DEX).

* * * * *